United States Patent [19]

Seager

[11] Patent Number: 5,183,055
[45] Date of Patent: Feb. 2, 1993

[54] DEVICE FOR OBTAINING TESTICULAR OR PENILE SIZE AND VOLUME MEASUREMENTS

[76] Inventor: Stephen W. J. Seager, 10301 Norton Rd., Potomac, Md. 20854

[21] Appl. No.: 813,655

[22] Filed: Dec. 27, 1991

[51] Int. Cl.$^5$ .............................................. A61B 5/103
[52] U.S. Cl. ..................................... 128/774; 33/512; 33/830
[58] Field of Search ................. 128/774, 782; 33/792, 33/809, 813, 818, 819, 830

[56] References Cited

U.S. PATENT DOCUMENTS

| | | | |
|---|---|---|---|
| 648,390 | 5/1900 | Coe | 33/813 |
| 3,114,976 | 12/1963 | Rantsch | 33/813 |
| 3,333,343 | 8/1967 | Elfast, Jr. | 33/512 |
| 4,097,997 | 7/1978 | Bjornson | 33/1 SD |
| 4,201,226 | 5/1980 | Phillips | 128/774 |
| 4,233,743 | 11/1980 | Flick | 128/774 |
| 4,312,363 | 1/1982 | Rothfuss et al. | 128/774 |
| 5,102,471 | 4/1992 | Sasaki | 136/244 |

FOREIGN PATENT DOCUMENTS

| | | | |
|---|---|---|---|
| 268621 | 6/1989 | Fed. Rep. of Germany | 128/774 |
| 7306 | 11/1893 | Switzerland | 33/830 |
| 1281249 | 1/1987 | U.S.S.R. | 128/774 |

OTHER PUBLICATIONS

Seager, "Pediatric Testicular Chart and Testicular Volume Chart" 2 pages, date unknown.

Primary Examiner—Max Hindenburg
Assistant Examiner—Guy V. Tucker
Attorney, Agent, or Firm—J. Gibson Semmes

[57] ABSTRACT

A device which is useful in urological and andrological measurements of anatomical organs and for calculation of related volumetric capacity thereof which includes a graduated rule, bearing at one end thereof a fixed jaw, the rule defining an elongated cavity therein with a rack on at least one side thereof, and a movable jaw marker assembly opposed to the fixed jaw, said assembly being slideably mounted upon the rule; a refined marker scale engaging the rule in operative connection, and including a drive to motivate the refined scale relative to the graduated scale of the rule.

2 Claims, 1 Drawing Sheet

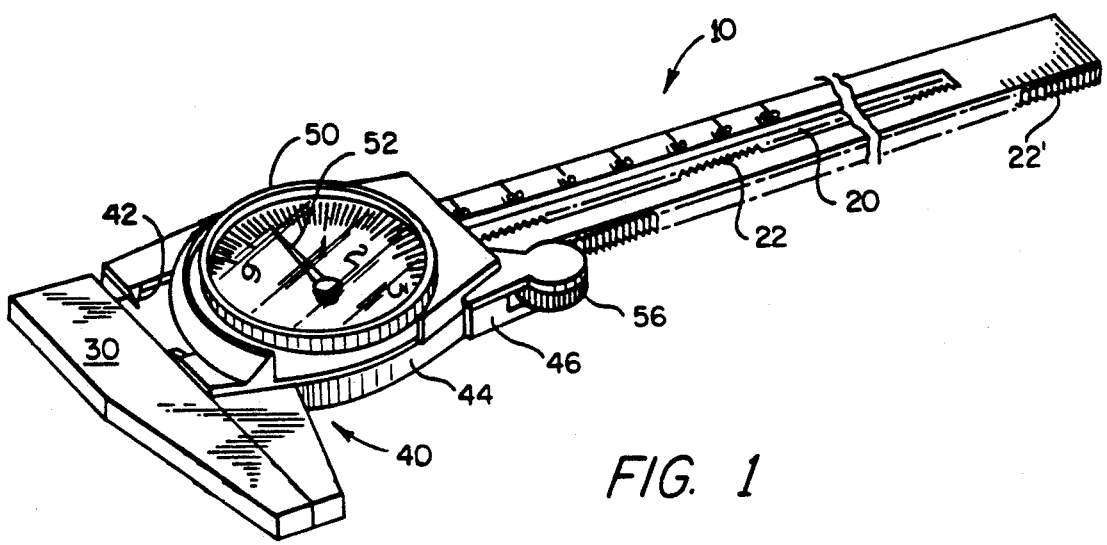
FIG. 1
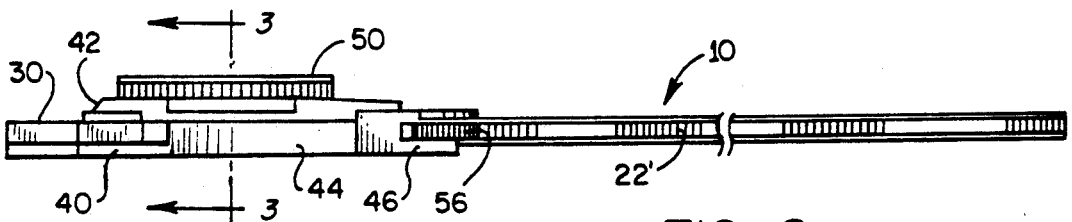
FIG. 2
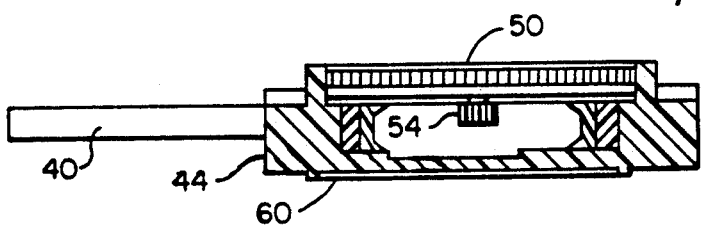
FIG. 3
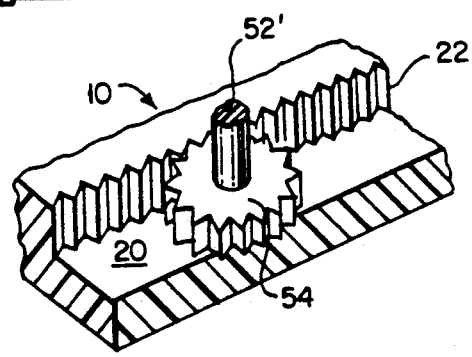
FIG. 4
| Testicular Volume (cc) | Length → |  |  |  |  |  |  |  |  |
|---|---|---|---|---|---|---|---|---|---|
| cm | 3.0 | 3.2 | 3.4 | 3.6 | 3.8 | 4.0 | 4.2 | 4.4 | 4.6 |
| 3.0 | 14.1 | 15.1 | 16.0 | 17.0 | 17.9 | 18.8 | 19.8 | 20.7 | 21.7 |
| 2.8 | 12.3 | 13.1 | 14.0 | 14.8 | 15.6 | 16.4 | 17.2 | 18.1 | 18.9 |
| 2.6 | 10.6 | 11.3 | 12.0 | 12.7 | 13.5 | 14.2 | 14.9 | 15.6 | 16.3 |
| 2.4 | 9.0 | 9.7 | 10.3 | 10.9 | 11.5 | 12.1 | 12.7 | 13.3 | 13.9 |
| 2.2 | 7.6 | 8.1 | 8.6 | 9.1 | 9.6 | 10.1 | 10.6 | 11.2 | 11.7 |
| 2.0 | 6.3 | 6.7 | 7.1 | 7.5 | 8.0 | 8.4 | 8.8 | 9.2 | 9.6 |
| 1.8 | 5.1 | 5.4 | 5.8 | 6.1 | 6.4 | 6.8 | 7.1 | 7.5 | 7.8 |
FIG. 5

DEVICE FOR OBTAINING TESTICULAR OR PENILE SIZE AND VOLUME MEASUREMENTS

BACKGROUND OF THE INVENTION

There has long been a need in clinical medicine and research for a tool to accurately measure testicular/penile size and volume characteristics. With the recent medical emphasis on male andrology, the need has become more acute. It is a well-documented fact that in both human and animal medicine, there is a direct relationship between testicular size/volume, and sperm and quality count. Other aspects of fertility are also related to testicular/penile size. The measuring device hereinafter defined is used to obtain testicular/penile length and width. Utilizing a computer calculated formula, the volume of each testicle is calculated; accordingly, records may be maintained for accurate reference on individual patient charts.

The present device herein reduces many of the disadvantages experienced with other testicular measuring devices. Its utility may be extended to other functions, hereinafter noted. The coined term "ORCHOMETER" refers to the measuring device comprising the invention. It is a coined word based upon the word "Orchis".

SUMMARY OF INVENTION

Apparatus for obtaining selective measurement of the male testicles and/or penis, in a clinical environment. It is useful in both adult and pediatric urology and andrology.

The apparatus comprises a graduated rule having a fixed outer jaw and a rack defined therein. A movable jaw marker is opposed. A refined marker scale is mounted upon the opposed jaw with rotary manual drive means thereon; this forms a part of the refined marker scale which engages the rule to generate refined measurement.

BRIEF DESCRIPTION OF THE DRAWINGS

FIG. 1 is a view in perspective of the measuring apparatus in its closed and portable condition.

FIG. 2 is a partial view in side elevation of the apparatus illustrated in FIG. 1.

FIG. 3 is a vertical section view of the apparatus of FIGS. 1 and 2, taken along lines 3—3 of FIG. 2.

FIG. 4 is a fragmentary perspective of the rule and micrometer of FIG. 1.

FIG. 5 is a planned view of the FIG. 3 chart comprising a comparator scale.

DESCRIPTION OF PREFERRED EMBODIMENTS

To conduct the present clinical practice of urology and/or andrology, the equipment defined herein is utilized. It is broadly illustrated in FIG. 1, wherein the following components are combined in a unitary construction.

The measurement instrument consists of a rule 10 wherein its upper surface is graduated in fixed millimeter gradation increments of 10. The rule has an uppermost cavity 20, said groove forming a rack 22 on the near wall thereof. Rack 22 is adapted to engagement by a corresponding drive pinion 54 of the refined meter 50 wherein increments are in 0.1 mm gradations.

On the left end of the rule 10 is a fixed jaw 30, said jaw 30 being adjacent a zero measure abutment for a corresponding movable jaw assembly 40, said jaw defining opposed markers 42. Movable jaw assembly 40 bears a rule engaging slide 44 and its extension 46. Extension 46 forms a journal for a rule engaging manual drive 56. Both drives 54 and 56 are coplanar relative to each other, reference FIGS. 2 & 3.

Superposed upon the jaw 40 is the micrometric meter 50, wherein there is defined a circular 0.1 mm scale with pointer 52 and an axial extension 52', FIG. 4. Extension gear pinion 54 has rotary meshing engagement with the corresponding rack 22 of cavity 20 of rule 10. On the far extension 46 of the rule engaging slide assembly 40 is drive pinion 56 which engages corresponding rack 22', formed on the near exterior of rule 10. Drive 56 is loosely journaled. Its function is to refine the incremental measurements between jaws 30-40, reference scale 50. Pinions 54 & 56 are respectively driven and driving the latter causing movements to and fro of the joint assembly 40.

On the reverse side of the rule 10 is a comparator scale 60 wherein the capacitive testicular (cc) volume per patient may be computed graphically by width-length measurements from the instrument. See FIG. 3 and chart below.

OPERATION
Testicular Volume (cc)

| Width ↓ | cm Length → 3.0 | 3.2 | 3.4 | 3.6 | 3.8 | 4.0 | 4.2 | 4.4 | 4.6 |
|---|---|---|---|---|---|---|---|---|---|
| 3.0 | 14.1 | 15.1 | 16.0 | 17.0 | 17.9 | 18.8 | 19.8 | 20.7 | 21.7 |
| 2.8 | 12.3 | 13.1 | 14.0 | 14.8 | 15.6 | 16.4 | 17.2 | 18.1 | 18.9 |
| 2.6 | 10.6 | 11.3 | 12.0 | 12.7 | 13.5 | 14.2 | 14.9 | 15.6 | 16.3 |
| 2.4 | 9.0 | 9.7 | 10.3 | 10.9 | 11.5 | 12.1 | 12.7 | 13.3 | 13.9 |
| 2.2 | 7.6 | 8.1 | 8.6 | 9.1 | 9.6 | 10.1 | 10.6 | 11.2 | 11.7 |
| 2.0 | 6.3 | 6.7 | 7.1 | 7.5 | 8.0 | 8.4 | 8.8 | 9.2 | 9.6 |
| 1.8 | 5.1 | 5.4 | 5.8 | 6.1 | 6.4 | 6.8 | 7.1 | 7.5 | 7.8 |

Please refer to chart for further data

OPERATION

There is defined herein an ideal measurement device for determining, in a clinical situation, testicular size and volume in both adult and pediatric urology and andrology. Testicular measurements are made by extending the testicle into the scrotum until a firm testicular outline is seen through the scrotum wall. In testicular width measurement, the Orchometer jaws are opened, placed on the testicle and the jaws reduced until the scrotal skin adjacent to the testicle is very slightly indented. Testicular length is measured in a similar fashion.

The Orchometer may also be used for measuring penile size and volume both in tumescence and detumescence for a number of diagnostic evaluations. For example, one may evaluate the effect of penile injectables or vacuum pump devices to obtain an erection. Likewise, one may measure pediatric clinics to document growth patterns.

In addition, scrotal skin measurements assist in correlating the thickness of the scrotal skin and the possible effect on thermal conductivity in the fertility evaluation. Such measurements are undertaken by gently extending the scrotum between thumb and forefinger in a downward or lateral direction, depending on the position of the patient. Once a normal tension has been reached, thickness of the scrotum raphe is measured. This measurement can vary from 0.2 to 0.7 mm.

I claim:

1. A hand manipulable device which is useful in determining urological and andrological clinical measurement of one or more organs of the anatomy and for calculation of related volumetric capacity thereof, comprising:

a) a graduated rule having fixed gradations embossed in an upper surface thereof, the rule terminating at one end in an anatomy contacting fixed jaw, said rule having an elongated cavity therein with a first rack defined on at least one side of the cavity; a second rack being defined on an outside edge of the rule, both said racks being coplanar and parallel to each other;

b) a movable jaw assembly in opposed measurement relation to the fixed jaw, the movable jaw bearing markers for the fixed gradations of the rule, on an anatomy contacting end thereof;

c) a refined marker meter superposed on the movable jaw assembly, in driven engagement with the first rack of the rule, said meter including a first pinion, engaging said first rack for activating a marker of the refined meter, relative to the fixed gradations of the rule;

d) a second pinion on the movable jaw assembly in constant engageable contact with the second rack, the second pinion being rotateable by a user to apply incremental movements to the movable jaw assembly and the refined marker meter, relative to the gradations of the rule; both said pinions being coplanar, relative to each other.

e) a comparator chart on the measurement device whereby capacitive testicular volume may be computed by width-length measurements obtained from the device.

2. The hand manupulable device of claim 1 wherein the rule per se defines metric gradations and the marker meter is graduated in tenths of the metric gradations.

* * * * *